(12) United States Patent
Nie et al.

(10) Patent No.: US 11,369,369 B2
(45) Date of Patent: Jun. 28, 2022

(54) LINEAR STAPLER WITH ADJUSTMENT MECHANISM

(71) Applicants: EZISURG MEDICAL CO., LTD., Shanghai (CN); Ezisurg (Suzhou) Medical Co. Ltd., Jiangsu (CN)

(72) Inventors: Honglin Nie, Shanghai (CN); Shan Huang, Shanghai (CN); Jun Yang, Shanghai (CN); Anhua Li, Shanghai (CN); Guang Yang, Shanghai (CN); Jidong Chen, Shanghai (CN)

(73) Assignees: EZISURG MEDICAL CO., LTD., Shanghai (CN); EZISURG (SUZHOU) MEDICAL CO. LTD., Jiangsu (CN)

( * ) Notice: Subject to any disclaimer, the term of this patent is extended or adjusted under 35 U.S.C. 154(b) by 0 days.

(21) Appl. No.: 16/638,036

(22) PCT Filed: Jul. 9, 2018

(86) PCT No.: PCT/CN2018/094987
§ 371 (c)(1),
(2) Date: Feb. 10, 2020

(87) PCT Pub. No.: WO2019/029307
PCT Pub. Date: Feb. 14, 2019

(65) Prior Publication Data
US 2020/0214698 A1 Jul. 9, 2020

(30) Foreign Application Priority Data

Aug. 11, 2017 (CN) .......................... 201710687426.2

(51) Int. Cl.
*A61B 17/072* (2006.01)
*A61B 17/068* (2006.01)
(Continued)

(52) U.S. Cl.
CPC ........... *A61B 17/068* (2013.01); *A61B 17/115* (2013.01); *A61B 2017/0046* (2013.01);
(Continued)

(58) Field of Classification Search
CPC .......... A61B 2017/0725; A61B 17/072; A61B 17/07207
(Continued)

(56) References Cited

U.S. PATENT DOCUMENTS 4,608,981 A * 9/1986 Rothfuss .......... A61B 17/07207
227/180.1
5,074,454 A * 12/1991 Peters .............. A61B 17/07207
227/178.1
(Continued)

FOREIGN PATENT DOCUMENTS

CN 103169513 A 6/2013
CN 203122501 U 8/2013
(Continued)

OTHER PUBLICATIONS

International Search Report and Written Opinion dated Sep. 27, 2018 in International Application PCT/CN2018/094987.

*Primary Examiner* — Gloria R Weeks
(74) *Attorney, Agent, or Firm* — Venable LLP

(57) ABSTRACT

This application provides a linear stapler with an adjusting mechanism having wider adjusting scope and more suitable pressing force and being more convenient to operate, and including an adjusting shift lever with at least one step surface on each of upper and lower ends, an adjusting slider with multiple step surfaces on an end surface close to the adjusting shift lever, and an adjusting chassis having multiple step surfaces on an end surface close to the adjusting shift lever. The adjusting shift lever rotates with a shifted adjusting knob to generate relative displacement vertical to
(Continued)

the step surface with the adjusting slider at one end and relative displacement vertical to the step surface with the adjusting chassis at the other end, and drive a nail abutting seat subassembly to rotate relatively to a nail bin seat, until the thickness of clamped tissue is consistent in near and far ends.

11 Claims, 4 Drawing Sheets

(51) Int. Cl.
  *A61B 17/115* (2006.01)
  *A61B 17/00* (2006.01)
(52) U.S. Cl.
  CPC ............. *A61B 2017/00663* (2013.01); *A61B 2017/07278* (2013.01); *A61B 2017/07285* (2013.01)
(58) Field of Classification Search
  USPC ............................................ 227/175.1, 181.1
  See application file for complete search history.

(56) References Cited

U.S. PATENT DOCUMENTS

| | | | |
|---|---|---|---|
| 5,111,987 A | | 5/1992 | Moeinzadeh et al. |
| 7,334,717 B2* | | 2/2008 | Rethy ................... A61B 17/105 227/175.1 |
| 7,905,381 B2* | | 3/2011 | Baxter, III ........ A61B 17/07207 227/180.1 |
| 9,370,359 B2* | | 6/2016 | Johnson ............ A61B 17/07207 |
| 10,667,818 B2* | | 6/2020 | McLain ............ A61B 17/07207 |
| 10,687,819 B2* | | 6/2020 | Stokes ................ A61B 17/115 |
| 10,905,419 B2* | | 2/2021 | Schings ............ A61B 17/07207 |
| 2004/0267311 A1* | | 12/2004 | Viola ............... A61B 17/07207 606/219 |
| 2014/0014705 A1* | | 1/2014 | Baxter, III ......... A61B 17/0644 227/175.1 |
| 2020/0315620 A1* | | 10/2020 | Nie ..................... A61B 17/072 |

FOREIGN PATENT DOCUMENTS

| | | |
|---|---|---|
| CN | 203138588 U | 8/2013 |
| CN | 105832372 A | 8/2016 |
| CN | 107456254 A | 12/2017 |
| EP | 3469995 A1 | 4/2019 |

* cited by examiner

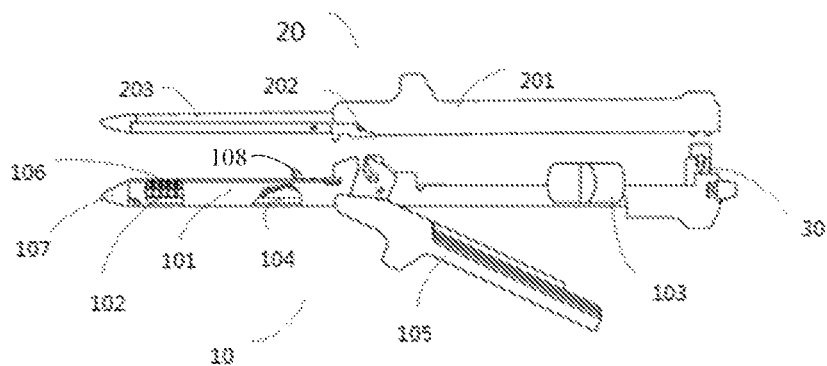
FIG. 1
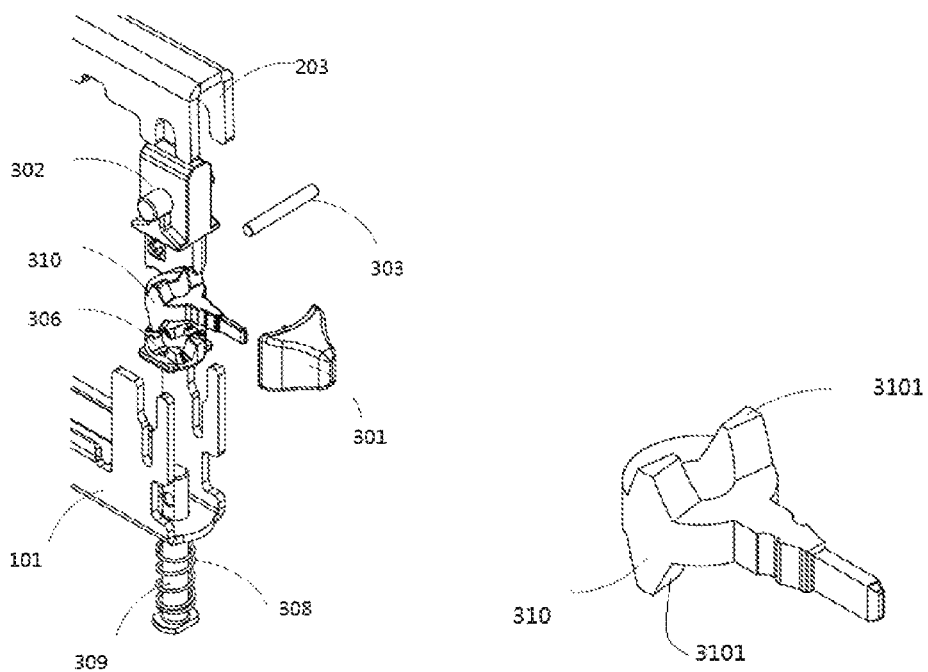
FIG. 2
FIG. 3

LINEAR STAPLER WITH ADJUSTMENT MECHANISM

CROSS REFERENCE TO RELATED APPLICATION

This application is a national stage application, filed under 35 U.S.C. § 371, of International Application No. PCT/CN2018/094987, filed on Jul. 9, 2018, entitled "LINEAR STAPLER WITH ADJUSTMENT MECHANISM," which claims priority to Chinese Patent Application No. 201710687426.2 filed on Aug. 11, 2017, which is incorporated herein by reference in its entirety.

TECHNICAL FIELD

The present application relates to a linear stapler, and particularly relates to a linear stapler with an adjusting mechanism.

BACKGROUND

At present, clinical application of linear staplers has already been quite popular. An action principle of linear staplers is that two handle subassemblies (generally, one handle includes a nail bin seat subassembly, and the other handle includes a nail abutting seat subassembly) get close to clamp a tissue, and then push out suturing nails in a nail bin of a stapler to take a shape and suture the tissue together. Some linear staplers have a cutting function and are provided with a cutter, and after a tissue is sutured, the cutter cuts off the sutured tissue.

A linear stapler with the foregoing function includes a first handle portion and a second handle portion, the first handle portion includes a nail bin seat subassembly, the second handle portion includes a nail abutting seat subassembly; the nail bin seat subassembly mainly includes detachable nail bin subassembly, locking lever and driving subassembly; the nail bin subassembly generally includes a nail bin, a plurality of suturing nails and a plurality of nail push blocks, wherein multiple rows of holes are formed in the nail bin, suturing nails are provided in the holes, and the upper surface of the nail bin is a tissue contact surface; the nail abutting seat subassembly mainly includes a nail abutting seat and a shell, the nail abutting seat includes a nail forming surface, and multiple rows of nail forming slots are formed in the nail forming surface. The nail bin seat subassembly and the nail abutting seat subassembly can be connected together, and are locked by the locking lever located on the nail bin seat subassembly, so as to close a to-be-sutured tissue. The driving subassembly includes a wedged push piece, and will drive suturing nails in the nail bin to take a shape in the nail forming slots in the nail forming surface of the nail abutting seat when moving from the near end of a stapler to a far end. Generally, a driving subassembly also includes a cutter, which is used for cutting a tissue among multiple rows of nail threads after the tissue is sutured by the suturing nail.

In existing design of linear staplers, when anastomosis is performed on different tissues, because tissue toughness and thickness are inconsistent, especially, stomach and lung, when anastomosis length is great (more than 75 mm), difference between the thicknesses of tissues at the far end and the near end of a surgical spot is more obvious, as a result, when the stapler closes relatively thick or thin tissues, the compressed thickness of the clamped tissues at the near end and the far end will generate a phenomenon of being inconsistent. When the closed tissue is relatively thick, a phenomenon that the compressed thickness at the far end is greater than that at the near end will be caused, as shown in FIG. 7, in closing, tissue thickness at the far end is L2, tissue thickness at the near end is L1, at the moment L2>L1, such situation will cause inconsistent height of formed nails of suturing nails at the near end and the far end, the formed nail at the far end is too high, and even is poor in forming, which will further cause the phenomena of suture bleeding, anastomotic leakage and the like. When the closed tissue is relatively thin, a phenomenon that the compressed thickness at the far end is smaller than that at the near end will be caused, as shown in FIG. 8, at the moment, L2<L1, such situation also will cause inconsistent height of formed nails of suturing nails at the near end and the far end, and the formed nail at the far end is too low, further causing tissue damage at the far end.

Patent application No. 201610345074.8 titled: "A surgical stapler", and incorporated herewith by reference in its entirety discloses an adjustable stapler, in which an adjusting mechanism is provided between a first handle portion and a second handle portion, so that the second handle portion generates rotation relative to the first handle portion by a rotating shaft thereof, and then the thickness of a clamped tissue is consistent at the near end and the far end. However, an adjustable scope of the adjusting mechanism is limited, an adjusting operation is inconvenience, and pressing force to a tissue after adjusting is hard to control.

SUMMARY

In order to solve the foregoing technical problem, the present application provides a linear stapler with an adjusting mechanism, so that the thickness of a clamped tissue is consistent at the near end and the far end, to increase the suture nail forming yield, and reduce the phenomena of suture bleeding, anastomotic leakage and the like. The linear stapler provided by the present application has a wide adjusting scope and more suitable pressing force and is more convenient to operate in comparison with adjusting mechanisms in the prior art.

A linear stapler provided according to the present application includes: a first handle portion, a second handle portion and an adjusting mechanism, the first handle portion and the second handle portion being assembled together; the first handle portion including a nail bin seat subassembly, the nail bin seat subassembly including a nail bin seat; the second handle portion including a nail abutting seat subassembly, and the nail abutting seat subassembly including a nail abutting seat.

The adjusting mechanism is provided between the nail bin seat subassembly and the nail abutting seat subassembly, and includes an adjusting knob, an adjusting slider, an adjusting shift lever, an adjusting chassis, a rotating screw and a compressed spring; the adjusting chassis is connected with the nail bin seat subassembly by the rotating screw and the compressed spring; the adjusting slider is connected with the nail abutting seat subassembly; and the adjusting shift lever is located between the adjusting chassis and the adjusting slider.

The adjusting knob is connected with the adjusting shift lever, the adjusting shift lever has at least one step surface on each of an upper end and a lower end, the adjusting slider has at least three different step surfaces on an end surface close to the adjusting shift lever, the adjusting chassis has at least three different step surfaces on an end surface close to the adjusting shift lever; a step surface at one end of the adjusting shift lever is engaged with a step surface on the adjusting slider, a step surface at the other end of the adjusting shift lever is engaged with a step surface on the adjusting chassis; and when an adjusting knob is shifted, the adjusting shift lever rotates therewith, so that the adjusting shift lever generates relative displacement in a direction vertical to the step surface with the adjusting slider at one end, and generates relative displacement in a direction vertical to the step surface with the adjusting chassis at the other end, and further drives a nail abutting seat subassembly to generate rotation relative to a nail bin seat, until the thickness of clamped tissue is consistent at the near end and the far end.

In a specific implementation mode, the nail bin seat subassembly also includes detachable nail bin subassembly, locking lever and driving subassembly; the nail bin subassembly including a nail bin, a plurality of nail push blocks and a plurality of suture nails; the locking lever being rotatably mounted on the nail bin seat, and the nail bin seat subassembly and the nail abutting seat subassembly being locked in a lengthwise direction by the locking lever after being assembled together.

Specifically, the driving subassembly includes a push knob, a triggering push piece and a cutter.

Further, a round hole are formed in the nail bin seat, the round hole being in coaxial match with the rotating screw, the adjusting chassis, the adjusting shift lever and the adjusting slider.

Further, the adjusting slider is connected with the nail abutting seat subassembly by a sliding pin.

Optimally, the adjusting mechanism is provided at the near end of the stapler.

Specially, the nail abutting seat subassembly also includes a nail abutting seat pin and a shell, the nail abutting seat having one nail forming surface.

In an optimal implementation mode, step surfaces on the adjusting slider and step surfaces on the adjusting chassis are arranged in one-to-one correspondence in a vertical direction.

Further, a highest step surface on the adjusting slider is aligned to a highest step surface on the adjusting chassis in a vertical direction, a medium step surface on the adjusting slider is aligned to a medium step surface on the adjusting chassis in a vertical direction, and a lowest step surface on the adjusting slider is aligned to a lowest step surface on the adjusting chassis in a vertical direction.

In an implementation mode, markers are set near the adjusting knob, to indicate the adjusting direction of the adjusting knob.

Optimally, an adjusting shift lever is made of metal, so that the adjusting shift lever is hard to deform and wear and is small in friction coefficient and easy to adjust and operate.

According to a linear stapler with an adjusting mechanism disclosed by the present application, by arranging an adjusting mechanism on a stapler, the thickness of a clamped tissue is consistent at the near end and the far end, to increase the suture nail forming yield, and reduce the phenomena of suture bleeding, anastomotic leakage and the like. Compared with staplers with adjusting mechanisms in the prior art, a linear stapler with an adjusting mechanism provided by the present application has an improved adjusting mechanism, in which step surfaces at the upper and lower ends of the adjusting shift levers are respectively in contact and engaged with step surfaces on the adjusting slider and the adjusting chassis, so that the adjusting shift lever is rotated to drive the adjusting shift lever to generate an effect of relative vertical movement on contact surfaces on the upper and lower ends.

In adjusting mechanisms of the prior art, two components directly generate vertical movement, that is, vertical movement is only generated on one contact surface, according to an improved adjusting mechanism in the present application, a difference value between steps is greater, and an adjusting scope is wider, so that a jaw at the far end of a handle of a stapler has a wider adjusting angle, to ensure that all tissues after normal operation are good in nail forming, and the situation of tissue necrosis cannot occur. Moreover, because viable tissues on a human body have blood pressure, and are better in elasticity, if pressing force in anastomosis is insufficient, tissue errhysis is easily caused after anastomosis, while an improved adjusting mechanism in the present application optimizes the pressing force, increases pressing force to tissues in operation and meanwhile ensures that tissues are not bruised after anastomosis. Moreover, a metal adjusting shift lever is added for an improved adjusting mechanism in the present application, so as to reduce resistance to the adjusting mechanism, increase operation conform and ensure the strength of the mechanism.

BRIEF DESCRIPTION OF THE DRAWINGS

FIG. 1 is a schematic structure diagram of a linear stapler according to an implementation mode of the present application;

FIG. 2 is a schematic structure diagram of an adjusting mechanism of the linear stapler in FIG. 1;

FIG. 3 is a schematic structure diagram of an adjusting shift lever of the adjusting mechanism in FIG. 2;

DESCRIPTION OF THE EMBODIMENTS

Figure 4:
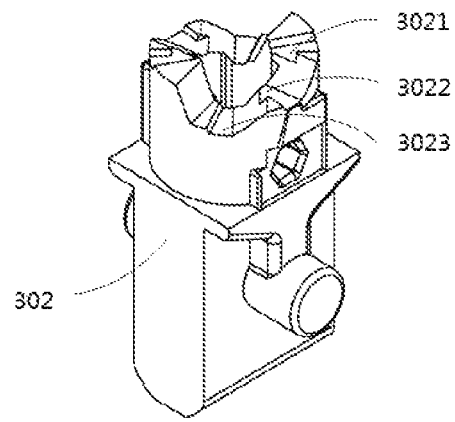
FIG. 4 is a schematic structure diagram of an adjusting slider of the adjusting mechanism in FIG. 2.

The following clearly and completely describes the technical schemes in the embodiments of the present invention, apparently, the described embodiments are merely some of the embodiments of the present invention rather than all of the embodiments. All other embodiments obtained by a person of ordinary skill in the art based on the embodiments of the present invention without creative efforts shall fall within the protection scope of the present disclosure.

For the convenience of description, "near end" in the whole application refers to an end close to an operator after the operator holds an instrument, and "far end" refers to an end far away from the operator after the operator holds the instrument.

Referring to FIGS. 1-6, the present application discloses a linear stapler with an adjusting mechanism, including: a first handle portion 10, a second handle portion 20 and an adjusting mechanism 30.

In the present embodiment, the first handle portion 10 includes a nail bin seat subassembly, and the second handle portion 20 includes a nail abutting seat subassembly.

Referring to FIG. 1, the nail bin seat subassembly includes detachable nail bin subassembly, nail bin seat 101, locking lever 105 and driving subassembly. The nail bin subassembly includes a nail bin 107, a plurality of nail push blocks 102 and a plurality of suture nails 106. The locking lever 105 is rotatably mounted on the nail bin seat 101. The driving subassembly includes a push knob 103, a triggering push piece 104 and a cutter 108.

Referring to FIG. 1, the nail abutting seat subassembly includes a nail abutting seat 203, a nail abutting seat pin 202 and a shell 201, wherein the nail abutting seat 203 has one nail forming surface.

The nail bin seat subassembly and the nail abutting seat subassembly can be assembled together and are locked in the lengthwise direction by the locking lever 105 on the nail bin seat subassembly.

The adjusting mechanism 30 is provided between the nail bin seat subassembly and the nail abutting seat subassembly, more specifically, between the nail bin seat 101 and the nail abutting seat 203.

Optimally, the adjusting mechanism 30 is provided at the near end of the stapler.

Referring to FIG. 2, the adjusting mechanism 30 includes an adjusting knob 301, an adjusting slider 302, an adjusting shift lever 310, an adjusting chassis 306, a rotating screw 309 and a compressed spring 308. The adjusting chassis 306 is connected with the nail bin seat subassembly by the rotating screw 309 and the compressed spring 308, and the adjusting slider 302 is connected with the nail abutting seat subassembly by a sliding pin 303. A round hole in the nail bin seat 101 is in coaxial match with the rotating screw 309, the adjusting chassis 306, the adjusting shift lever 310 and the adjusting slider 302, as shown in FIG. 2.

Figure 5:
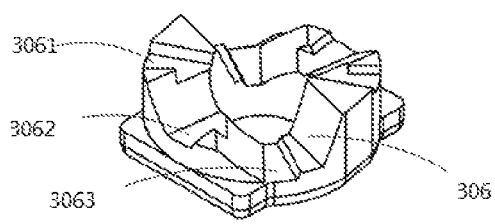
FIG. 5 is a schematic structure diagram of an adjusting chassis of the adjusting mechanism in FIG. 2.

An adjusting knob 301 and an adjusting shift lever 310 in the adjusting mechanism 30 are connected, and the adjusting knob 301 can be shifted to drive the adjusting shift lever 310 to rotate. Referring to FIG. 3, the adjusting shift lever 310 has at least one step surface 3101 on each of an upper end and a lower end. Refer to FIG. 2 and FIG. 4, the adjusting slider 302 has at least three different step surfaces 3021, 3022, 3023 on an end surface close to the adjusting shift lever 310. Refer to FIG. 2 and FIG. 5, the adjusting chassis 306 has at least three different step surfaces 3061, 3062, 3063 on an end surface close to the adjusting shift lever 310. Refer to FIG. 1, a step surface 3101 at the upper end of the adjusting shift lever 310 is engaged with a step surface on the adjusting slider 302, and a step surface 3101 at the lower end of the adjusting shift lever 310 is engaged with a corresponding step surface on the adjusting chassis 306. The adjusting slider 302 is connected with the nail abutting seat subassembly by a sliding pin 303.

Figure 9:
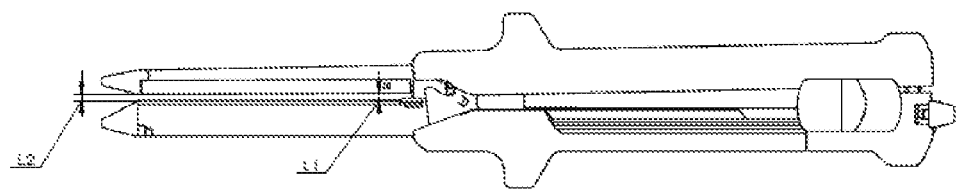
FIG. 9 is a schematic diagram after adjusting of the linear stapler of the present application in clamping a tissue.

The adjusting knob 301 can shift to the left and the right according to the thickness of a clamped tissue, and when the adjusting knob 301 is shifted, the adjusting shift lever 310 rotates therewith, and engaged step surfaces of the adjusting shift lever 310 and the adjusting slider 302 are changed, so as to generate displacement vertical to the direction of the step surfaces between the adjusting shift lever 310 and the adjusting slider 302, similarly, engaged step surfaces of the adjusting shift lever 310 and the adjusting chassis 306 are changed, so as to generate displacement vertical to the direction of the step surfaces between the adjusting shift lever 310 and the adjusting chassis 306. Relative displacement generated by the adjusting shift lever 310 in the upward direction and the downward direction causes the adjusting shift lever 310 and the adjusting slider 302 engaged with the adjusting shift lever 310 to generate displacement vertical to the direction of the step surface relative to the adjusting chassis 306 together, and further drives the nail abutting seat subassembly to generate rotation relative to the nail bin seat subassembly by the sliding pin 303, until the thickness of the clamped tissue is consistent at the near end and the far end, as shown in FIG. 9, at the moment L1=L2.

In an optimal implementation mode, step surfaces 3021, 3022, 3023 on the adjusting slider 302 and step surfaces 3061, 3062, 3063 on the adjusting chassis 306 are provided in one-to-one correspondence in a vertical direction, for example, a highest step surface 3021 on the adjusting slider 302 is aligned to a highest step surface 3061 on the adjusting chassis 306 in a vertical direction, a medium step surface 3022 on the adjusting slider 302 is aligned to a medium step surface 3062 on the adjusting chassis 306 in a vertical direction, and a lowest step surface 3023 on the adjusting slider 302 is aligned to a lowest step surface 3063 on the adjusting chassis 306 in a vertical direction. In adjusting, the adjusting knob 301 is shifted according to the thickness of a clamped tissue, so as to drive the adjusting shift lever 310 to rotate, to cause step surfaces 3101s on the adjusting shift lever 310 to be engaged with corresponding step surfaces on the adjusting slider 302 and the adjusting chassis 306.

For example, when the step surfaces 3101 on the adjusting shift lever 310 are engaged with the highest step surface 3021 on the adjusting slider 302 and the highest step surface 3061 on the adjusting chassis 306, a distance between the adjusting slider 302 and the adjusting chassis 306 is maximum. When the step surfaces 3101 on the adjusting shift lever 310 are engaged with the lowest step surface 3023 on the adjusting slider 302 and the lowest step surface 3063 on the adjusting chassis 306, a distance between the adjusting slider 302 and the adjusting chassis 306 is minimum.

Figure 6:
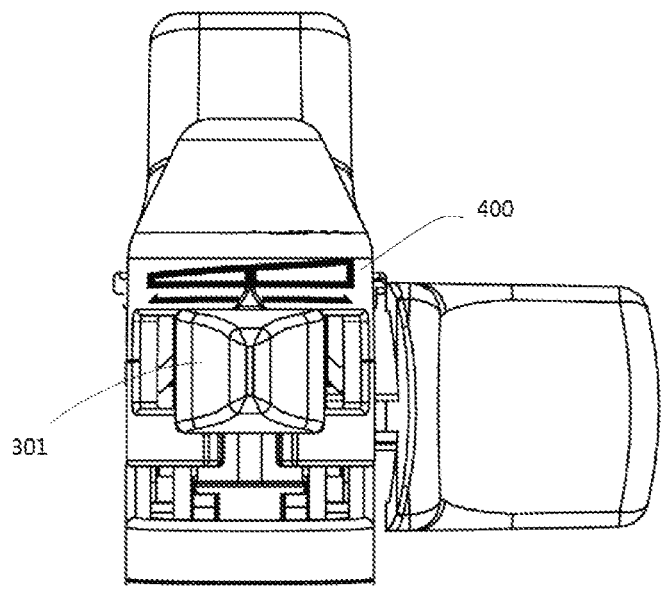
FIG. 6 is a schematic appearance diagram of an adjusting knob of the adjusting mechanism in FIG. 2.
Figure 7:
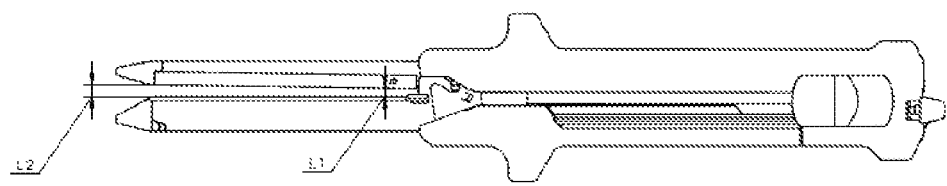
FIG. 7 is a schematic diagram before adjusting of the linear stapler of the present application in clamping a thick tissue.
Figure 8:
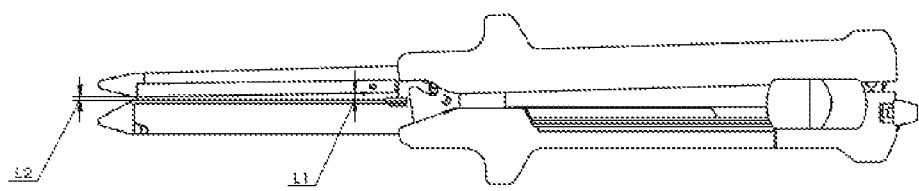
FIG. 8 is a schematic diagram before adjusting of the linear stapler of the present application in clamping a thin tissue.

As shown in FIG. 6, markers 400 may be set near the adjusting knob 301, to indicate the adjusting direction of the adjusting knob 301.

Further, the adjusting shift lever 310 is made of metal, and is hard to deform and wear, low in friction coefficient, and easy to adjust and operate.

According to the linear stapler with an adjusting mechanism of the present application, by arranging an adjusting mechanism on the stapler, the thickness of a clamped tissue is consistent at the near end and the far end, so as to increase the suture nail forming yield, and reduce the phenomena of suture bleeding, anastomotic leakage and the like. Compared with staplers with adjusting mechanisms in the prior art, the linear stapler with an adjusting mechanism of the present application has an improved adjusting mechanism, in which step surfaces at the upper end and the lower end of an adjusting shift lever are respectively in contact and engaged with step surfaces on the adjusting slider and the adjusting chassis, so that the adjusting shift lever is rotated to drive the adjusting shift lever to generate an effect of relative vertical movement on contact surfaces on the upper and lower ends. In adjusting mechanisms of the prior art, two components directly generate vertical movement, that is, vertical movement is only generated on one contact surface, according to an improved adjusting mechanism in the present application, a difference value between steps is greater, and an adjusting scope is wider, so that a jaw at the far end of a handle of a stapler has a wider adjusting angle, to ensure that all tissues after normal operation are good in nail forming, and the situation of tissue necrosis cannot occur. Moreover, because viable tissues on a human body have blood pressure, and are better in elasticity, if pressing force in anastomosis is insufficient, tissue errhysis is easily caused after anastomosis, while an improved adjusting mechanism in the present application optimizes the pressing force, increases pressing force to tissues in operation and meanwhile ensures that tissues are not bruised after anastomosis. Moreover, a metal adjusting shift lever is added for an improved adjusting mechanism in the present application, so as to reduce resistance to the adjusting mechanism, increase operation conform and ensure the strength of the mechanism.

It should be noted that implementation schemes in the accompanying drawings are merely representative embodiments of the present application, a person skilled in the art may easily understand that the protection scope of the present application is not merely limited in a scope defined by implementation modes in the accompanying drawings, and combination, transformation and variation for implementation modes in the drawings all fall within the protection scope of the present application.

The foregoing disclosed are merely several preferred embodiments of the present application, of course, the protection scope of the present application should be not limited hereby, therefore, equivalent variations made according to claims of the present application still belong to a coverage scope of the present application.

What is claimed is:

1. A linear stapler comprising:
a first handle portion including a nail bin seat;
a second handle portion including a nail abutting seat; and
an adjusting mechanism disposed between the nail bin seat and the nail abutting seat, the adjusting mechanism including an adjusting knob, an adjusting slider, an adjusting shift lever, an adjusting chassis, a rotating screw and a compressed spring, wherein
the adjusting chassis is connected with the nail bin seat via the rotating screw and the compressed spring, the adjusting slider is connected with the nail abutting seat, and the adjusting shift lever is located between the adjusting chassis and the adjusting slider, and wherein
the adjusting knob is connected with the adjusting shift lever, the adjusting shift lever having at least one step surface on each of an upper end and a lower end, the adjusting slider having at least three different step surfaces on an end surface adjacent to the adjusting shift lever, the adjusting chassis having at least three different step surfaces on an end surface adjacent to the adjusting shift lever, wherein a step surface at one end of the adjusting shift lever is engaged with a step surface on the adjusting slider, and a step surface at the other end of the adjusting shift lever is engaged with a step surface on the adjusting chassis.

2. The linear stapler according to claim 1, wherein the first handle portion further includes a locking lever and a driving subassembly, the locking lever being rotatably mounted on the nail bin seat, wherein the nail bin seat and the nail abutting seat are locked in a lengthwise direction by the locking lever after being assembled together.

3. The linear stapler according to claim 1, wherein a round hole is formed in the nail bin seat, the round hole being in coaxial match with the rotating screw, the adjusting chassis, the adjusting shift lever, and the adjusting slider.

4. The linear stapler according to claim 1, wherein the adjusting mechanism is provided at a near end of the stapler.

5. The linear stapler according to claim 4, wherein the adjusting mechanism is provided between the nail bin seat and the nail abutting seat.

6. The linear stapler according to claim 5, wherein step surfaces on the adjusting slider and step surfaces on the adjusting chassis are arranged in a one-to-one correspondence in a vertical direction.

7. The linear stapler according to claim 6, wherein a highest step surface on the adjusting slider is aligned to a highest step surface on the adjusting chassis in a vertical direction, and a lowest step surface on the adjusting slider is aligned to a lowest step surface on the adjusting chassis in a vertical direction.

8. The linear stapler according to claim 1, wherein the adjusting knob includes a marker which indicates an adjusting direction of the adjusting knob.

9. The linear stapler according to claim 1, wherein the adjusting shift lever is made of metal.

10. The linear stapler of claim 1, wherein shifting of the adjusting knob causes the adjusting shift lever to rotate, wherein the adjusting shift lever upon rotation generates a relative displacement in a direction vertical to the step surface with the adjusting slider at one end and generates another relative displacement in a direction vertical to the step surface with the adjusting chassis at the other end.

11. The linear stapler of claim 10, wherein the adjusting shift lever upon rotation drives the nail abutting seat to generate a rotation relative to the nail bin seat, until a thickness of clamped tissue is consistent at a near end and a far end of the linear stapler.

* * * * *